United States Patent [19]
Nishi et al.

[11] Patent Number: 5,345,515
[45] Date of Patent: Sep. 6, 1994

[54] METHOD AND APPARATUS FOR INSPECTING THE CLEANLINESS OF TOP SLIBERS

[75] Inventors: Noriyuki Nishi, Osaka; Tadashi Muto, Yamatokoriyama; Shinichi Takayama, Suzuka, all of Japan

[73] Assignee: Kanebo Ltd., Tokyo, Japan

[21] Appl. No.: 820,686

[22] PCT Filed: May 28, 1991

[86] PCT No.: PCT/JP91/00709
§ 371 Date: Mar. 18, 1992
§ 102(e) Date: Mar. 18, 1992

[87] PCT Pub. No.: WO91/19035
PCT Pub. Date: Dec. 12, 1991

[30] Foreign Application Priority Data

May 28, 1990 [JP] Japan ................... 2-139097

[51] Int. Cl.$^5$ .................... G06K 9/00; G01N 21/89
[52] U.S. Cl. ............................. 382/8; 382/1; 364/470; 356/238
[58] Field of Search .............. 382/1, 8; 356/238; 358/106, 107; 364/470

[56] References Cited

U.S. PATENT DOCUMENTS

| | | | |
|---|---|---|---|
| 3,524,988 | 8/1970 | Gaither | 356/238 |
| 3,887,814 | 6/1975 | Faulhaber | 356/238 |
| 4,430,720 | 2/1984 | Aemmes | 364/470 |
| 4,887,155 | 12/1989 | Massen | 358/107 |
| 5,134,568 | 7/1992 | Sainen | 364/470 |

FOREIGN PATENT DOCUMENTS 1143943 6/1989 Japan .

*Primary Examiner*—Leo H. Boudreau
*Assistant Examiner*—Chris Kelley
*Attorney, Agent, or Firm*—Armstrong, Westerman, Hattori, McLeland & Naughton

[57] ABSTRACT

A method of inspecting cleanliness of top sliber. The method classifies detected defects into pillwise defects and vegetal defects by introducing roundness, slenderness, gradation, dispersion, area, shape, gradation ratio, and length discernment against image signals of inspected top slibers picked up by an image sensor. An apparatus for inspecting cleanliness of top sliders is utilized. The apparatus initially picks up an image of uniformly spread top slibers conveyed to the apparatus and then processes the image signal with an image processing unit provided therefor. The method involves classifying defects on the top sliber into pillwise defects and vegetal defects in the top sliber based on the generated image signal. The classifying involves the steps of (i) establishing conditional section membership functions for features of defects, (ii) establishing conclusion section membership functions for determining a probability of being a defect against said classified defects, (iii) establishing a fuzzy rule for relating said features of defects with said probability of being a defect against the defects; and (iv) classifying the defects based on fuzzy reasoning derived from the conditional section membership functions, the conclusion section membership functions, and said fuzzy rule.

4 Claims, 20 Drawing Sheets

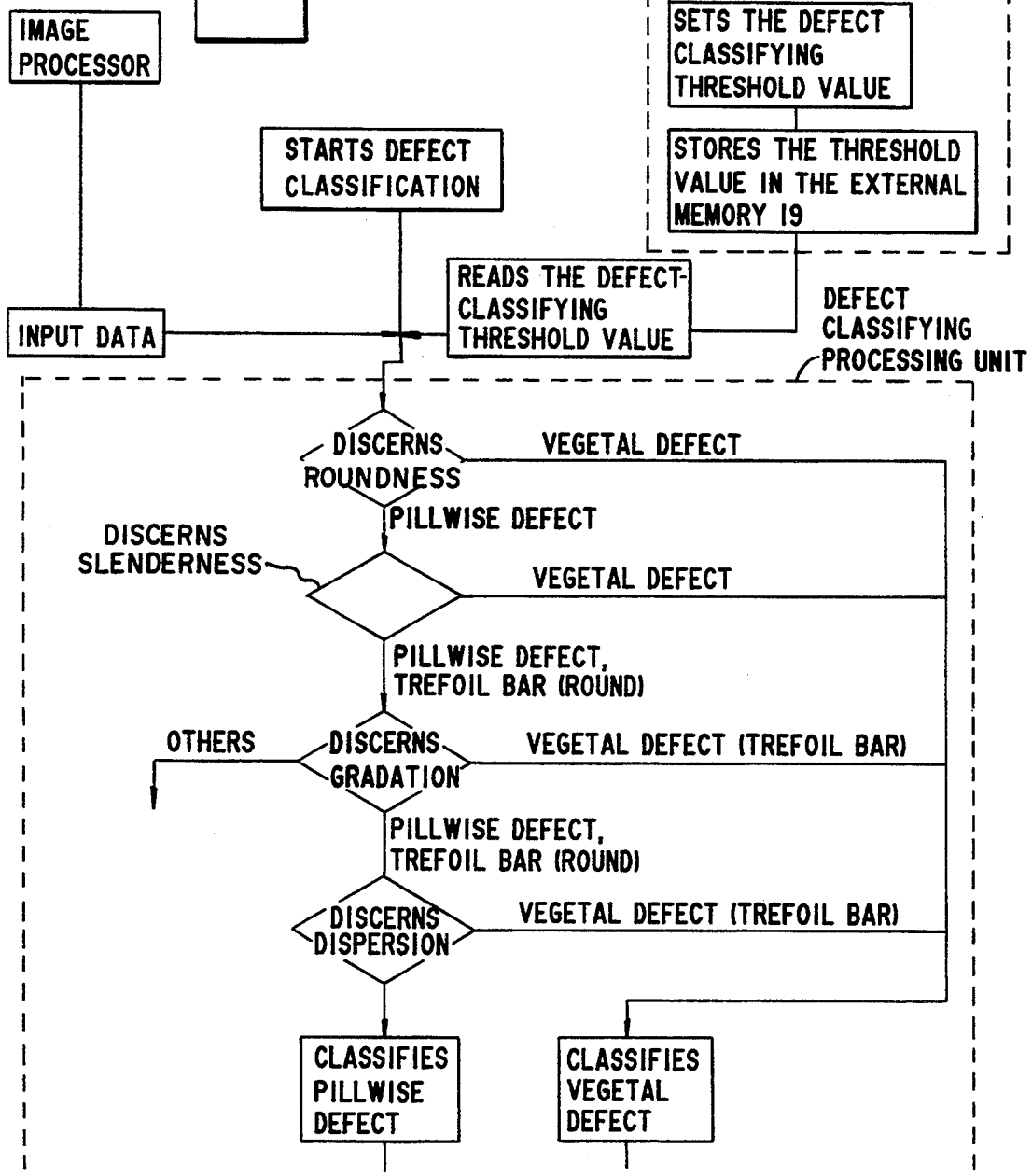

FIG.10
26 PILLWISE DEFECT
FIG.11
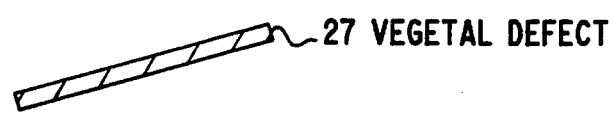
27 VEGETAL DEFECT
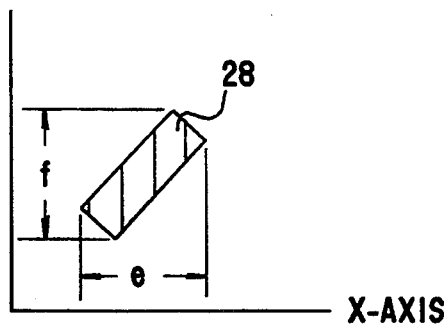
FIG.12
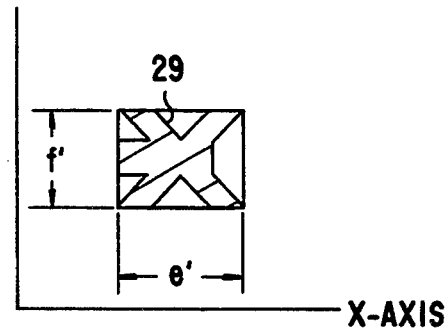
FIG.13

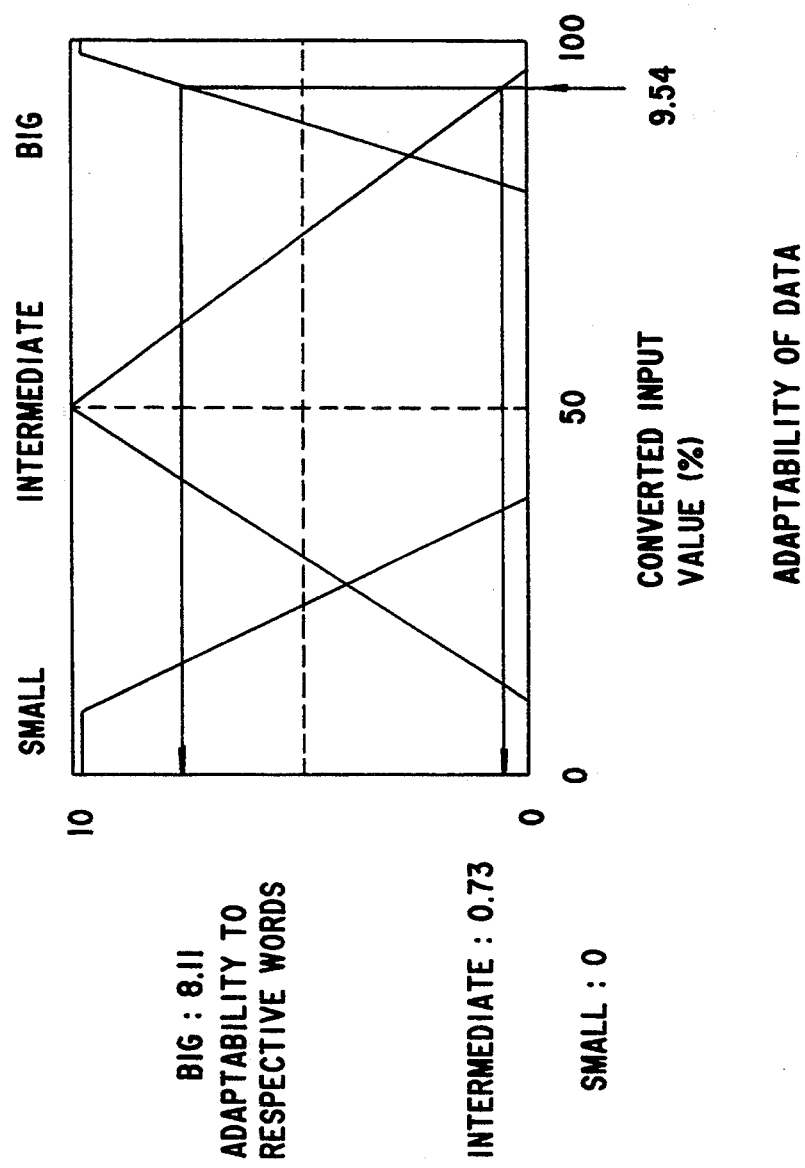

METHOD AND APPARATUS FOR INSPECTING THE CLEANLINESS OF TOP SLIBERS

BACKGROUND OF THE INVENTION

1. Field of the Invention

The present invention relates to a method and an apparatus for inspecting cleanliness of natural fiber tops, including wool and cotton for example.

2. Background Art

Normally, the inspection of the cleanliness of wool tops is executed in accordance with the inspection method prescribed in paragraph 5.6 (ruling the number of neps) and paragraph 5.7 (ruling the number of vegetal impurities) of JIS L-1083. The cleanliness is designated by means of the number of detected defects per inspection item present in a predetermined amount of inspected top sliber.

Conventionally, the cleanliness of wool top sliber is visually inspected. Authorized inspectors visually detect and classify defects from wool top slibers aligned on an inspection table. Conventionally, a specific continuous inspection method has been executed in accordance with paragraphs 5.6 and 5.7 of JIS L-1083 by thinly and uniformly spreading top slibers in a gill box by about 0.5 mm of thickness, and then, placing sampled top slibers on an inspection table. Inspectors then visually count the number of the impurities and defects by irradiating sampled top slibers with a light beam which is permeated through an inspection window. Since inspectors are obliged to visually count the number of impurities and defects based on the conventional practice, the results of visual inspection are noticeably varied between inspectors.

In order to minimize the difference of the inspected results, only strictly selected inspectors execute the inspection of the top slibers. Nevertheless, the resultant values are not yet reliable to a full extent. Actually, the visually inspected results are merely considered to be relative values of comparison.

In order to fully solve this problem, the Applicants of the invention had previously filed an application for a patent, as per the Japanese Patent Application No. 62-303563 of 1987, on a method of classifying pillwise defects and vegetal defects from an image signal generated from an image of top slibers picked up by an image sensor. This proposed inspection method introduced a system for discerning the elongation rate in the field of pillwise defects and vegetal defects. This in turn obliged the method to follow a complex computation to extract features of the defects. As a result of a slow speed available for the feature extracting process, the method could not properly be applied to the execution of continuous inspection processes.

OBJECT OF THE INVENTION

Therefore, the object of the invention is to provide an improved method and apparatus for precisely and very quickly inspecting the cleanliness of top slibers.

DISCLOSURE OF THE INVENTION

The method of inspecting the cleanliness of sampled top slibers embodied by the invention characteristically comprises a step for generating an image signal by picking up an image of top slibers with an image sensor and a step for classifying pill-wise defects and vegetal defects mixed in the inspected top slibers from the generated image signal based upon the discernment of the roundness and/or the discernment of the slenderness.

When executing a step for classifying defects, it is desired that the discernments of roundness, slenderness, gradation, and dispersion, be introduced. It is also possible for the method embodied by the invention to further classify the pillwise defect into slab, nep, and pinpoint defects based on the area discernment. In addition, the method embodied by the invention can further classify the vegetal defects into trefoil bars and those impurities and bars other than trefoil bars based on the shape discernment. In addition, the method embodied by the invention can further classify these impurities and bars based on the length discernment.

In the course of classifying those defects cited above, it is particularly effective for the method and apparatus embodied by the invention to execute the following sequential processes described below. Initially, the inspecting apparatus determines the range of a magnitude of the amount of features of respective defects. Next, the inspecting apparatus establishes "fuzzy rules" for classifying all of the defects by integrating two membership functions to determine the magnitude of the probability of being a particular defect out of all the defects and also to determine the adaptability of the respective defects to the range of the magnitude of the amount of those features of respective defects. Finally, the inspecting apparatus classifies all of the defects based on "fuzzy" reasoning derived from the membership functions and the "fuzzy rules".

The apparatus for inspecting cleanliness of top slibers embodied by the invention characteristically comprises the following: a gill box which spreads top slibers into a substantially uniform thickness and then externally delivers the spread top slibers, a plurality of rollers which respectively guide the spread top slibers, an illuminating unit which irradiates the spread top slibers with a light beam, an image sensor which picks up an image of the spread top slibers, a contact-free electrostatic removing unit which is installed to a position close to those rollers mentioned above and which eliminates static charge from the spread top slibers, and an image processing unit which processes an image signal from the image sensor.

BRIEF DESCRIPTION OF THE DRAWINGS

FIG. 3 through FIGS. 7(A) and 7(B) illustrate the steps in the method of processing the image of the inspected top slibers;

FIGS. 9(A) and 9(B) present an operating flowchart illustrating the flow of operations for classifying the cleanliness of the inspected top slibers shown in FIG. 8;

FIG. 10 through FIG. 13 are explanatory illustration of a variety of defects and the method of measuring the particular amounts of the features of the respective defects;

FIG. 29 graphically illustrates the method of determining adaptability to the particular amounts of the features of the respective defects;

DESCRIPTION OF THE PREFERRED EMBODIMENTS

Optimal Form for Embodying Invention

Referring now more particularly to the accompanying drawings, detail the method of and apparatus for inspecting cleanliness of top sliber according to an embodiment of the invention is described below.

Figure 1:
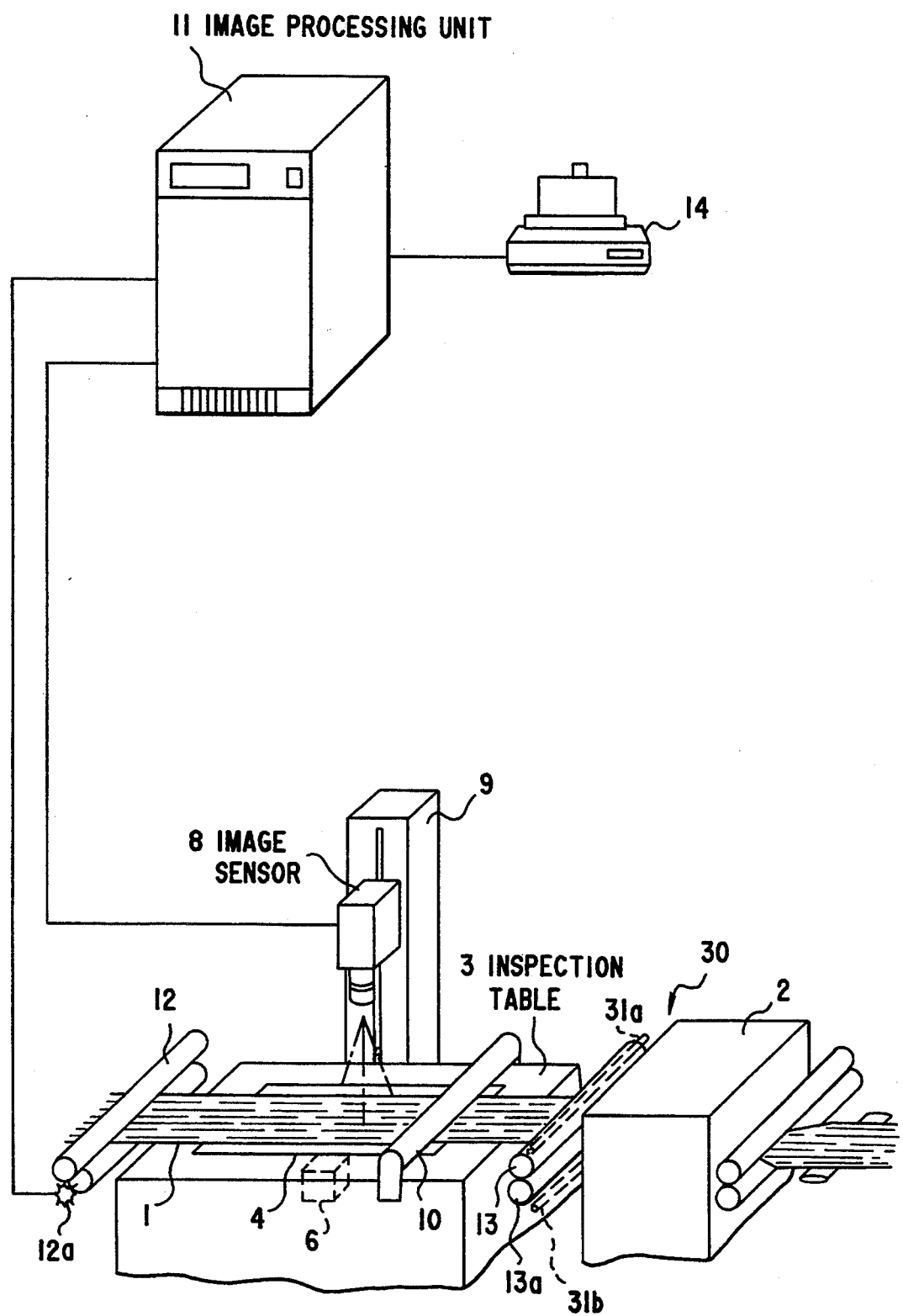
FIG. 1 presents an overall perspective view of the top inspection apparatus embodied by the invention.

FIG. 1 presents an overall perspective view of the top of the cleanliness inspection apparatus according to an embodiment of the invention. An image sensor (which is substantially a CCD camera) 8 is held by a supporting rod 9 and is secured to a position above an inspection window 4 of an inspection table 3. The image sensor 8 picks up an image of the sampled top sliber which is continuously delivered from a gill box 2. An illuminating unit 6 installed below the inspection window 4 emits a light beam upward. A roller 10 is installed in front of the image pickup position. The roller 10 prevents the top sliber 1 from superficially incurring a fluffing symptom.

An electrostatic preventing unit 30 is provided in the vicinity of a pair of guide rollers 13 and 13a which are respectively installed to the outlet of the gill box 2. The electrostatic preventing unit 30 consists of a rod 31a which is opposite from the upper guide roller 13 and another rod 31b which is opposite from the lower guide roller 13a. A high voltage is delivered to these rods 31a and 31b to permit the needle tips of these rods to respectively execute corona discharge in order to ionize ambient air before eliminating static charge from the charged object in a contact-free condition.

Next, the image of the top sliber 1 picked up by the image sensor 8 is then converted into an image signal before being delivered to an image processing unit 11. Simultaneously, synchronizing signals needed for continuously picking up the image are transmitted to the image processing unit 11 from a synchronizing sensor 12a secured to a measuring roller 12 which is set to a position close to the rear end of the inspection table 3.

The image processing unit 11 extracts a predetermined amount of the features, and then, based on the extracted feature data, the image processing unit 11 classifies the inspected top sliber 1 into respective degrees of cleanliness. Finally, the classified result is printed out by a printer 14 so that the result can be made available for the table designating the concrete results of the inspection of the cleanliness.

Figure 2:
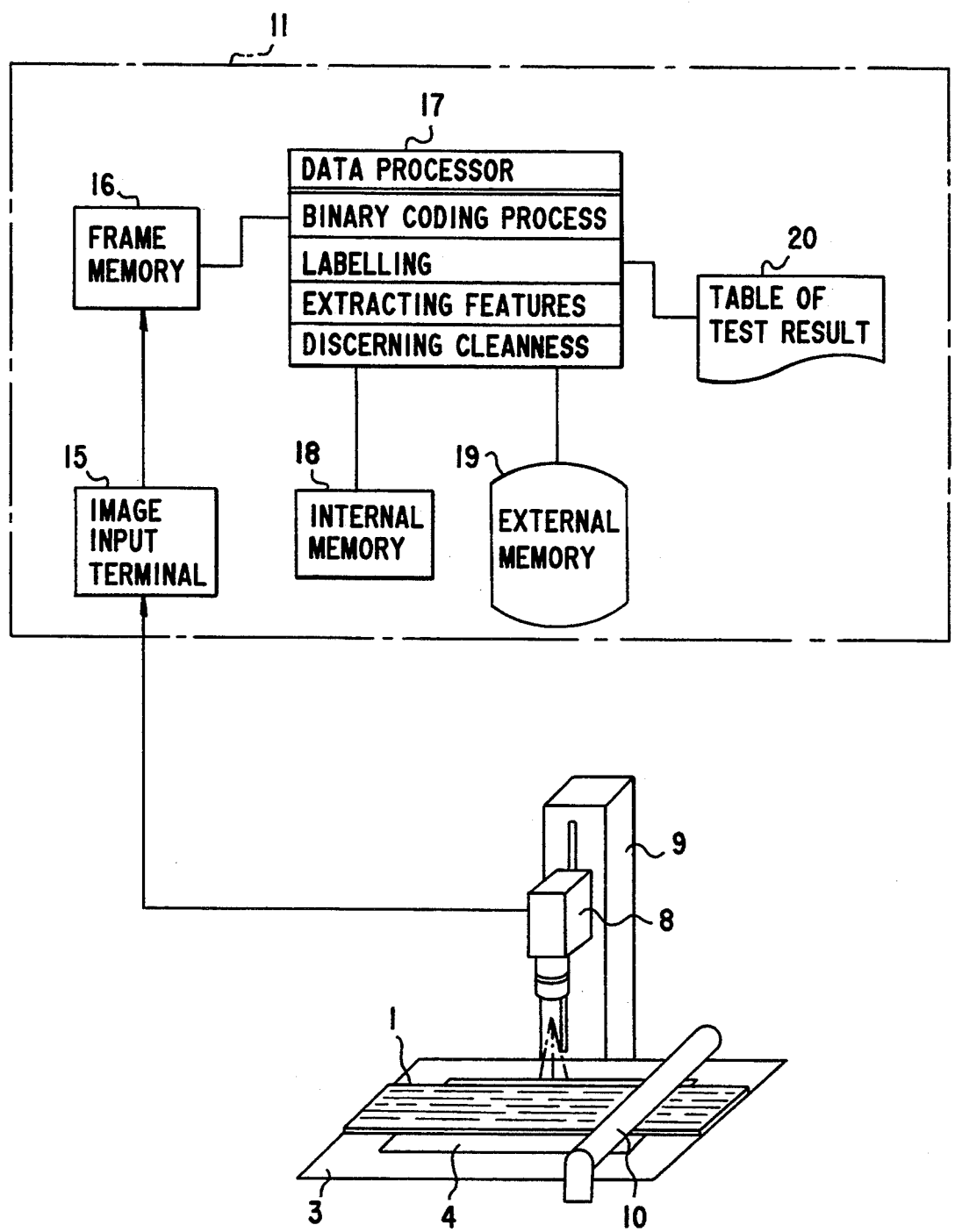
FIG. 2 is explanatory illustration of the operation of the image processing unit of the top inspection apparatus embodied by the invention.

FIG. 2 presents further details of the structure of the image processing unit 11. Structurally, the image processing unit 11 is composed of an image input terminal 15, a frame memory 16, a data processor 17, an internal memory 18, an external memory 19, and a system 20 available for printing the table of test results, respectively.

Figure 3:
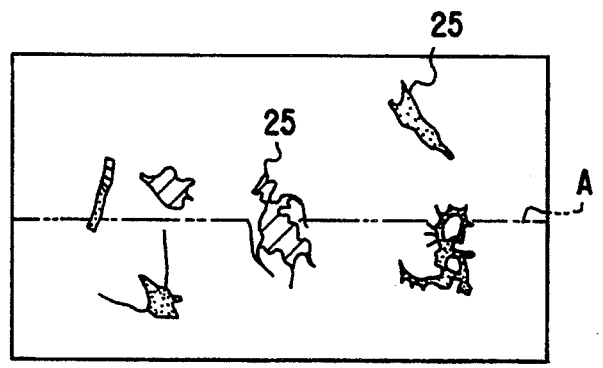
Figure 4:
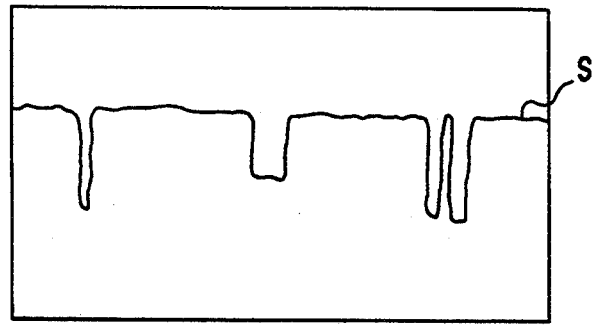
Figure 5:
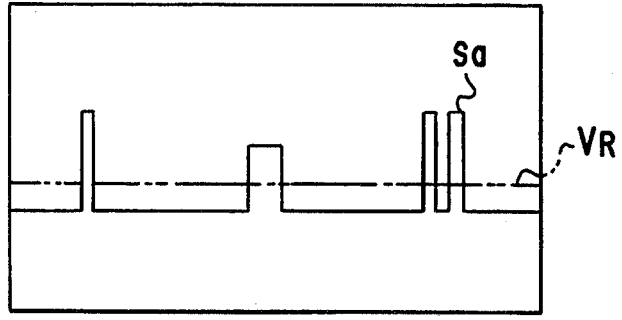
Figure 6:
Figure 7A:
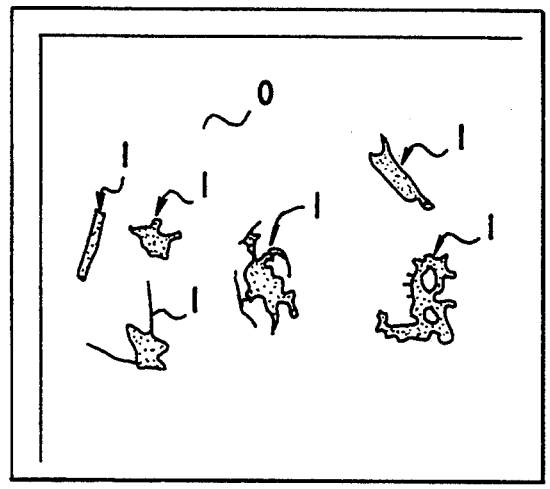
Figure 7B:
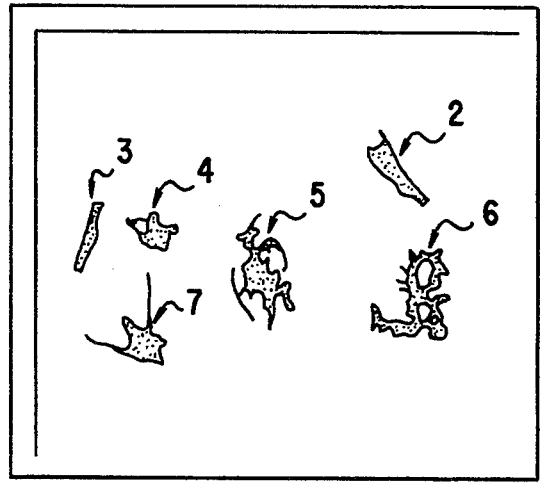

FIG. 3 illustrates a variety of images picked up by the image sensor 8. A variety of impurities and defects present in the sampled top sliber 1 are exposed to a light beam which is permeated from the inspection window 4, and then, according to the particular kinds of impurities and defects, these are converted into black shadows containing a depthwise gradation before eventually being caught by the image sensor 8. Next, the image containing the depthwise gradation is converted into an image signal "S" (shown in FIG. 4) before eventually being delivered to the image processing unit 11. The image signal shown in FIG. 4 corresponds itself to the image containing the depthwise gradation taken on line A. After being received by the image processing unit 11, the image signal "S" is converted by an A/D converter into a multivalent image signal "Sa" (shown in FIG. 5) by providing each picture element with a certain depth. The frame memory 16 stores this multivalent image signal "Sa". Next, the data processor 17 makes a comparison between the preset binary level and the multivalent image, as signal "Sa", and then generates a binary-coded image shown in FIG. 6. Next, the data processor 17 executes a pretreatment, in other words, a labelling operation, in order to secure the features present in the individual domains of the impurities and defects of the inspected top sliber 1 against the binary-coded image ("1" and "0" are the values given, as shown in the figure) shown in FIG. 7A, and then, as shown in FIG. 7B, the data processor 17 executes a numbering operation. Next, the data processor 17 computes the amount of features present in the numbered individual domains, and then stores the computed result in the internal memory 18. The apparatus embodied by the invention classifies the cleanliness of the inspected top sliber 1 based on the amount of the features of the defect.

Figure 8:
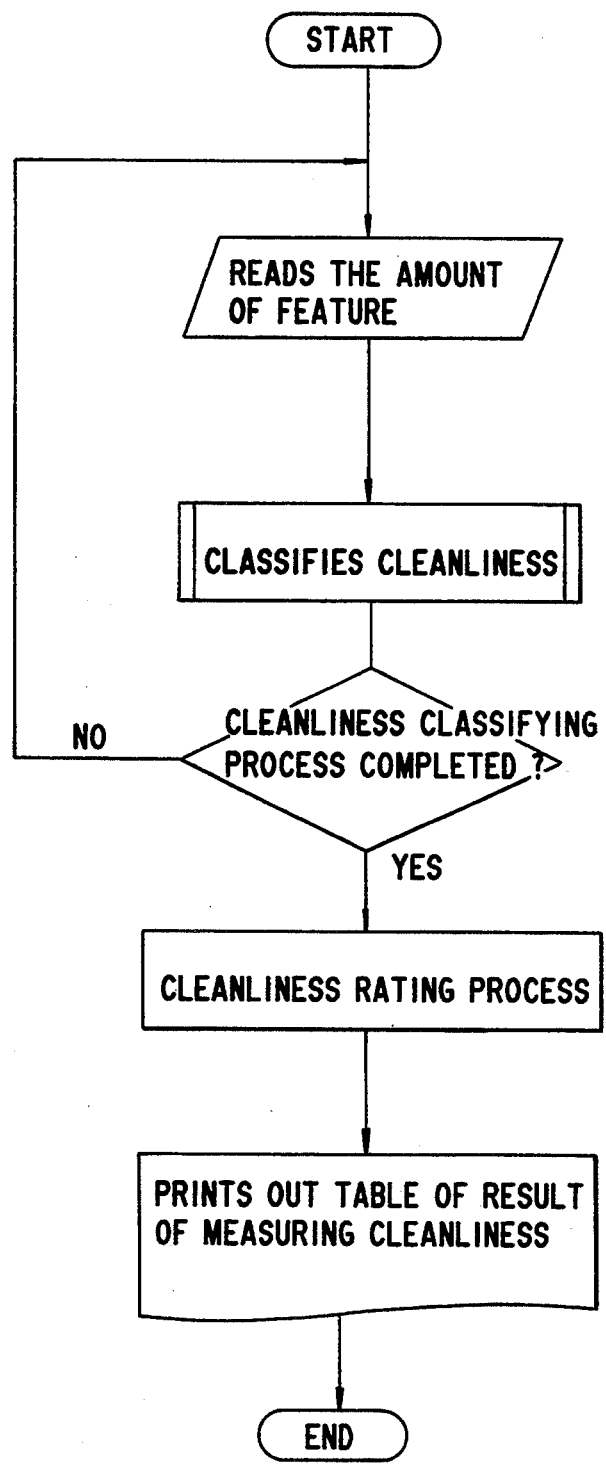
FIG. 8 presents an operating flowchart illustrating steps for processing the image of the inspected top slibers.

FIG. 8 presents an operating flowchart of the processes needed for discerning the cleanliness of the inspected top sliber 1. The data processor 17 reads the amount of the feature from the internal memory 18, and then classifies the cleanliness. After fully completing the process for classifying the cleanliness, the data processor 17 rates the cleanliness, and then prints the rated cleanliness on a table designating the inspected results. If the process for classifying cleanliness of the top sliber is not yet complete, then, the data processor 17 again reads the amount of the feature before eventually classifying the cleanliness of the inspected top sliber 1.

Figure 9B:
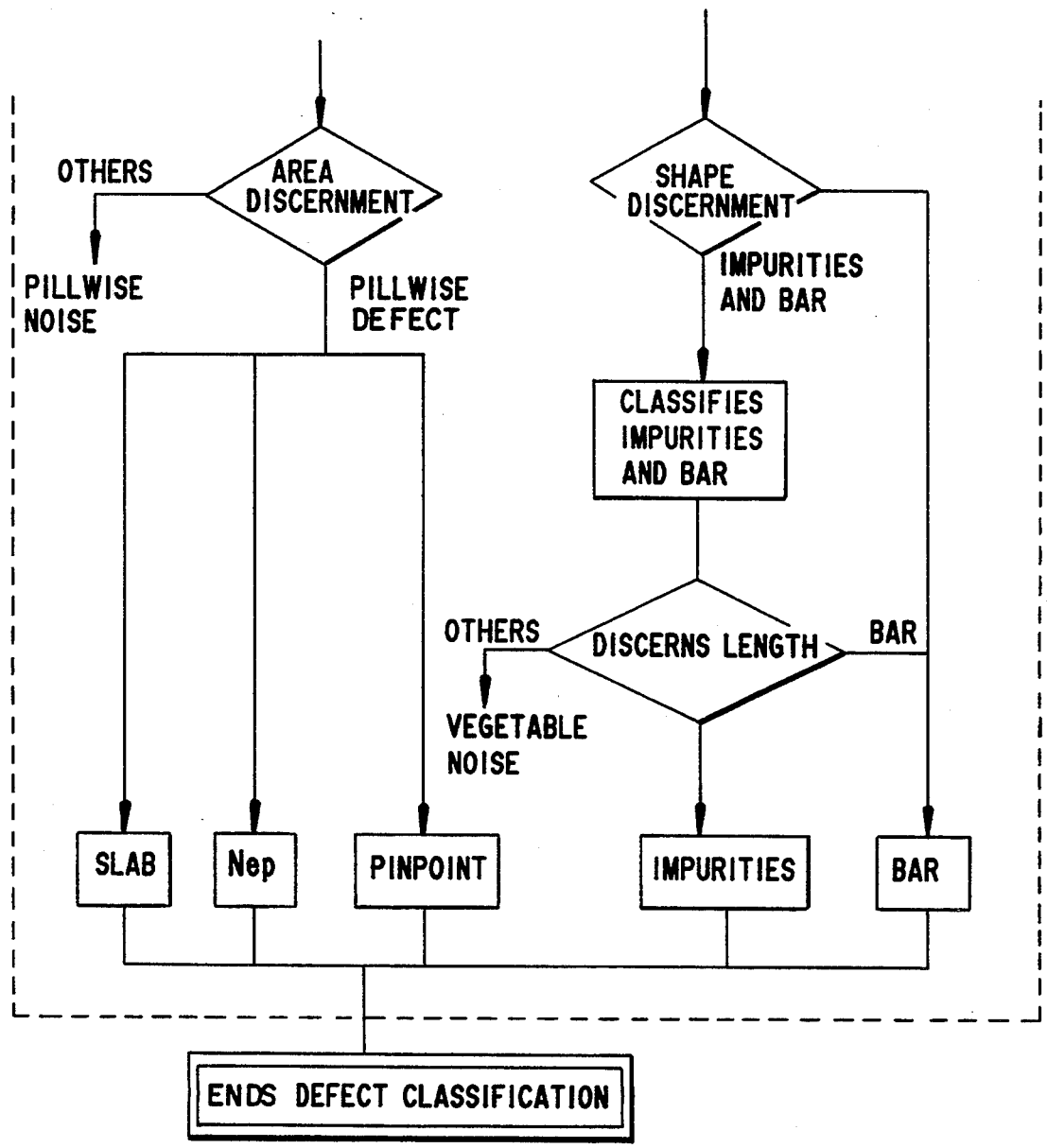
Figure 14:
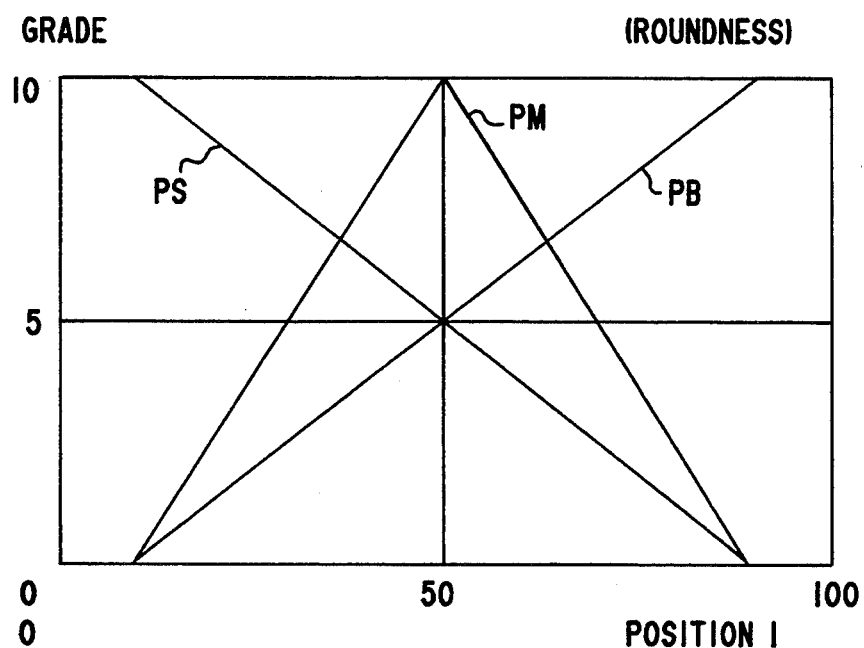
FIG. 14 through FIG. 20 particular graphically illustrate membership functions to determine the particular amounts of the features of the respective defects.
Figure 15:
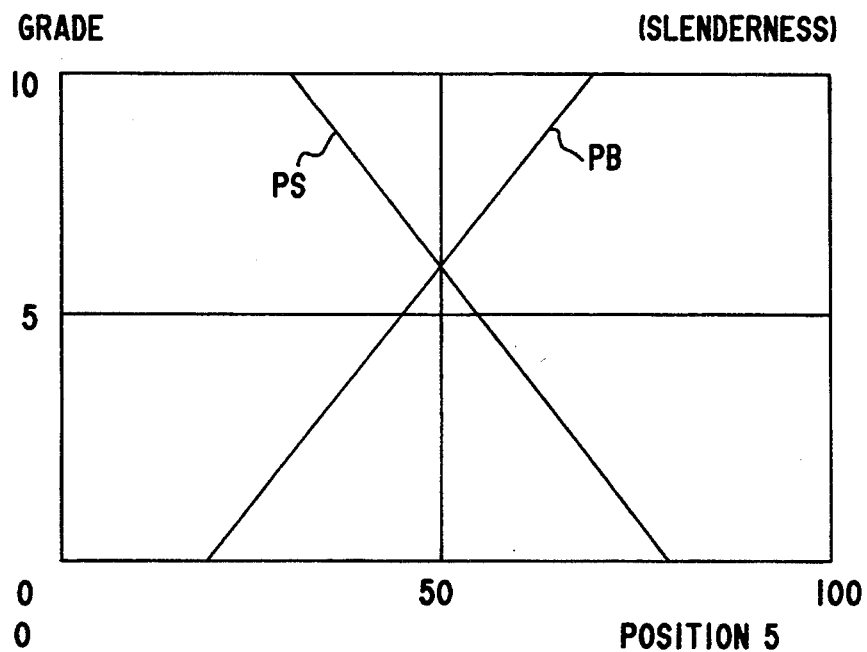
Figure 16:
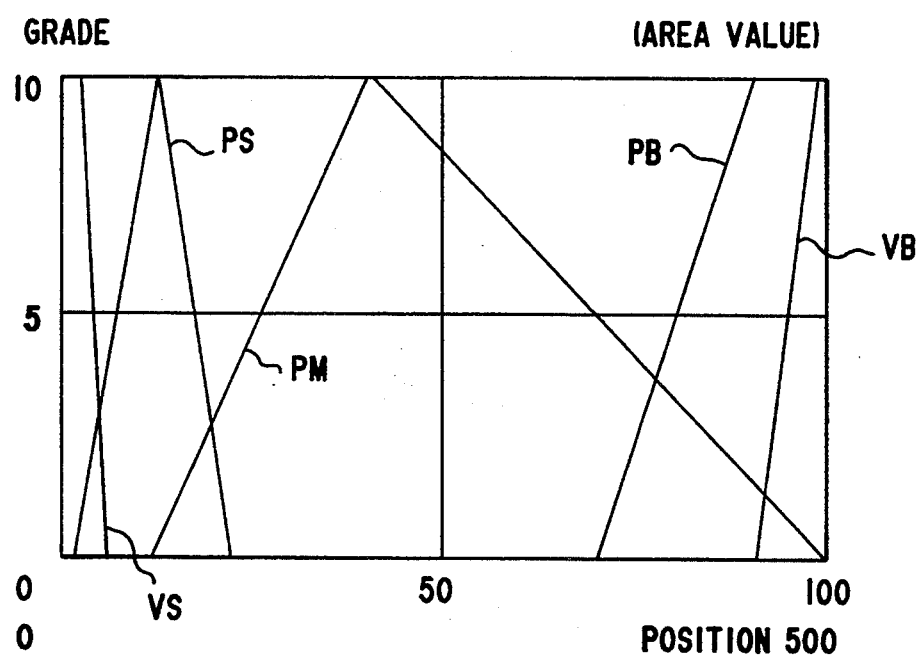
Figure 17:
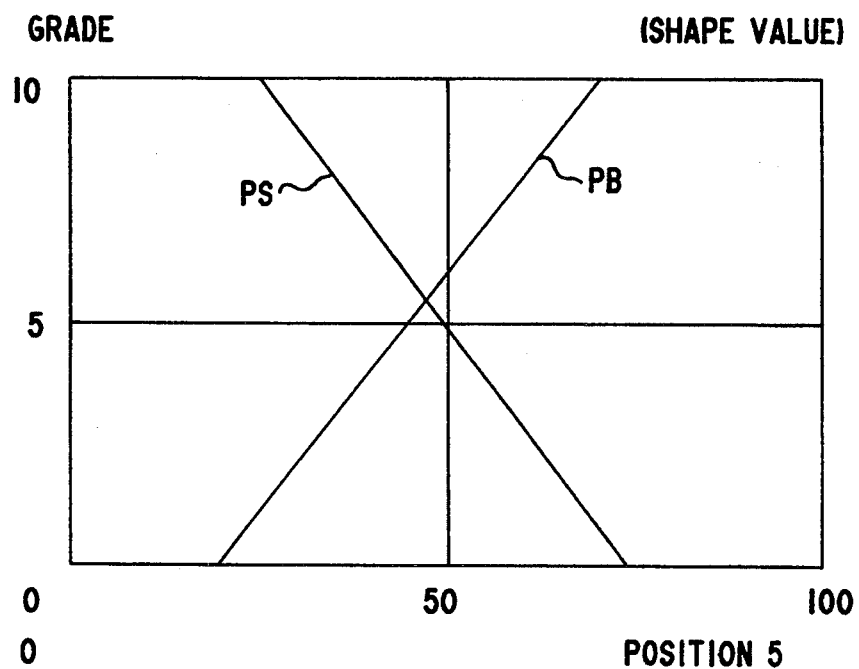
Figure 18:
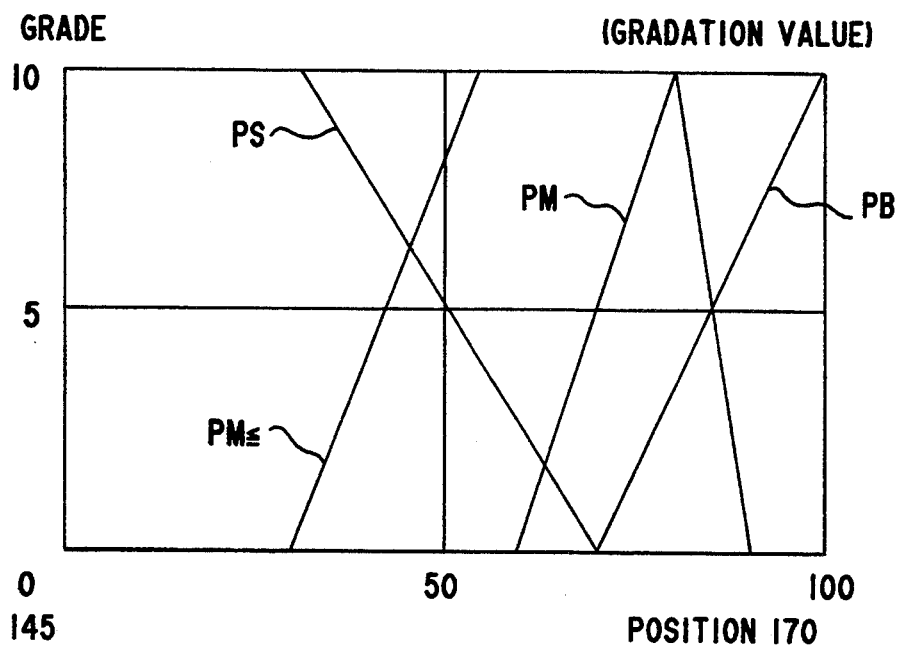
Figure 19:
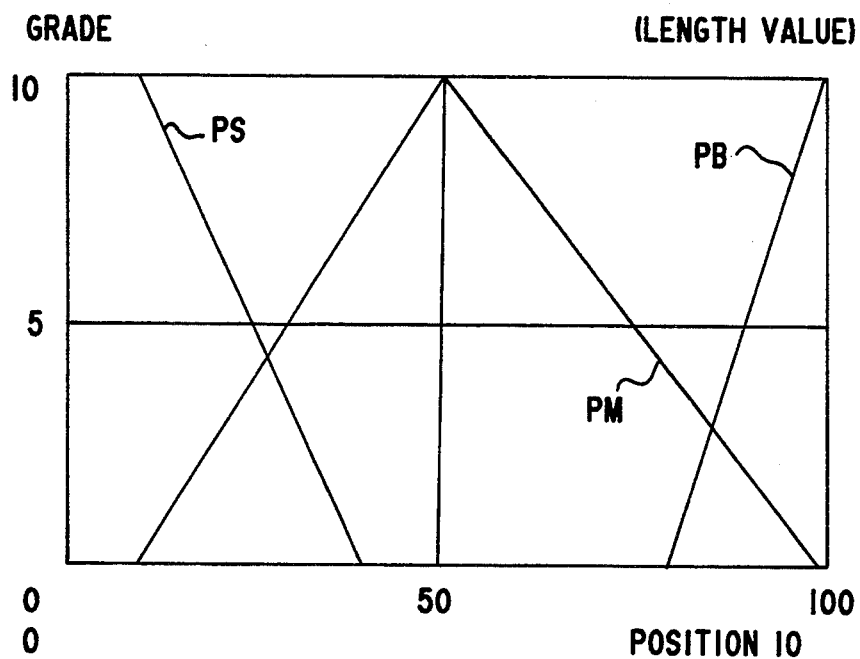
Figure 20:
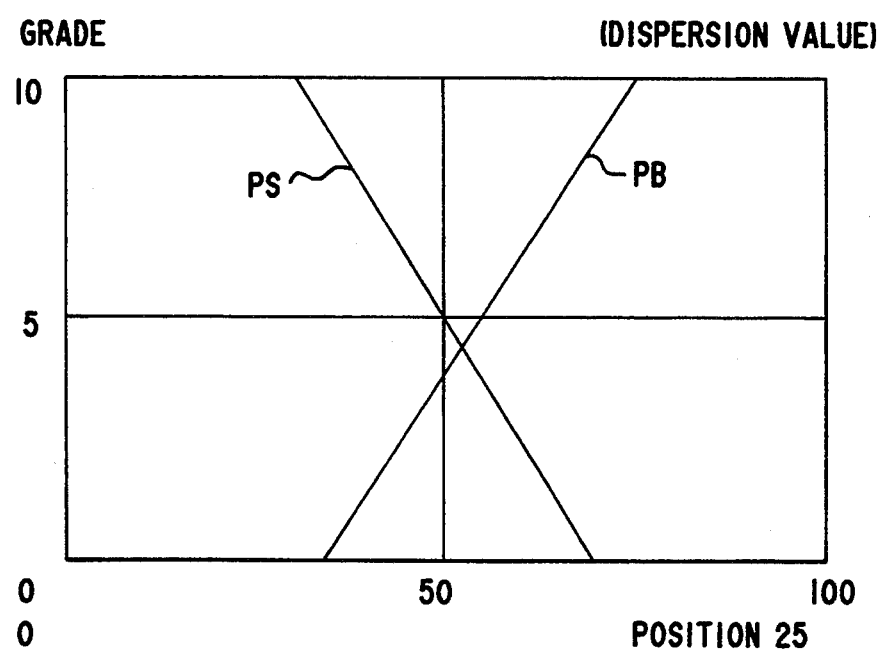
Figure 21:
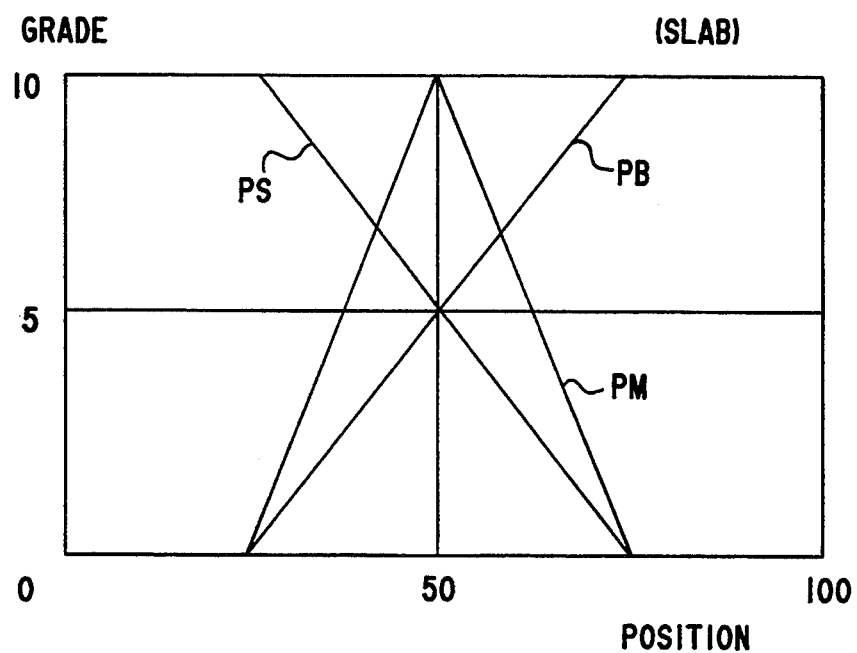
FIG. 21 through FIG. 28 graphically illustrating membership functions to deal with the respective defects.
Figure 22:
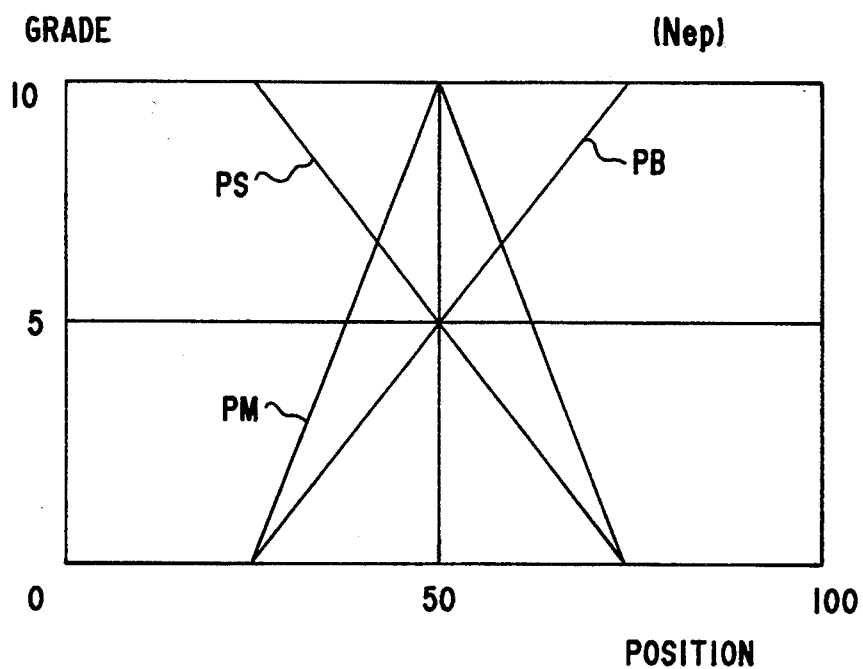
Figure 23:
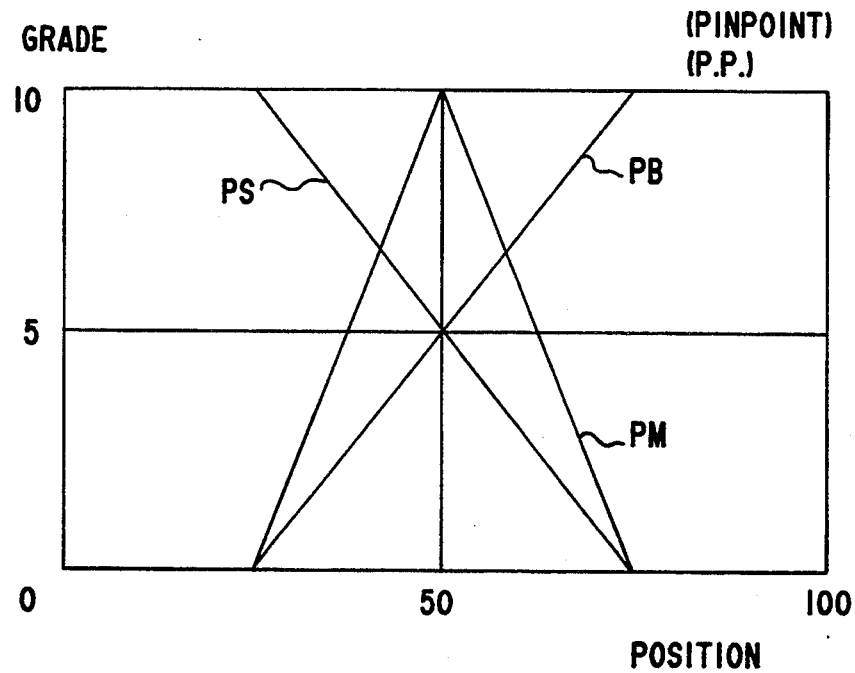
Figure 24:
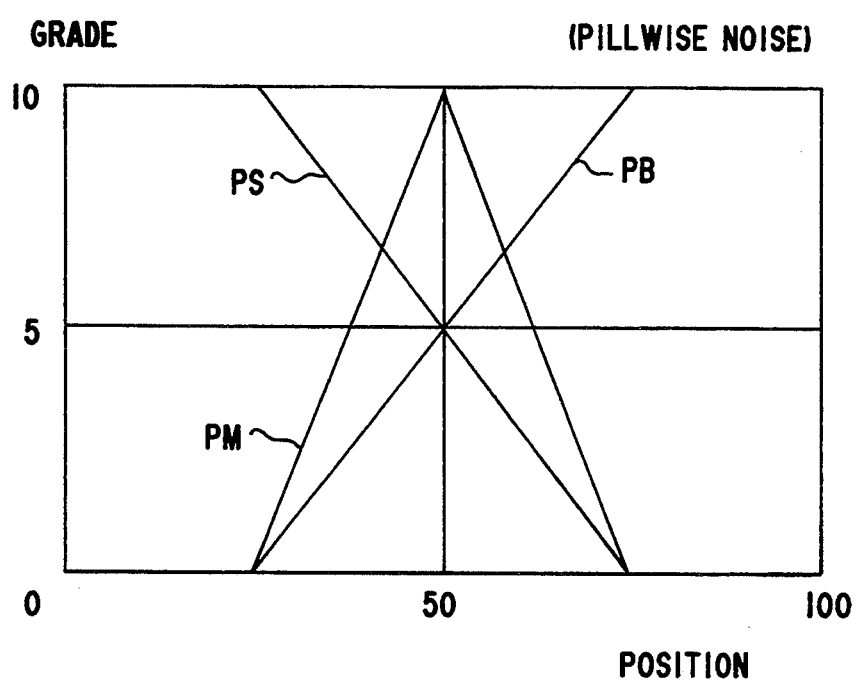
Figure 25:
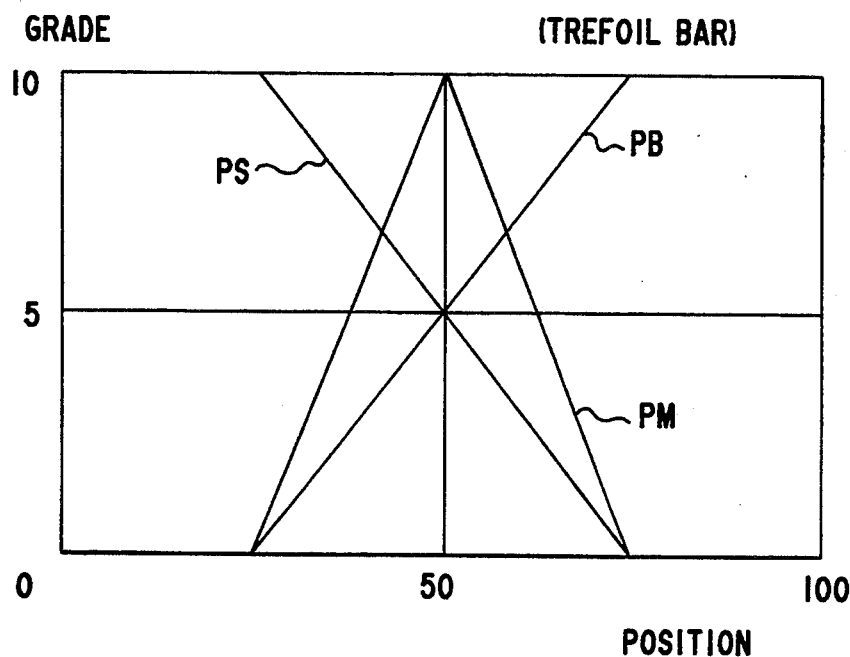
Figure 26:
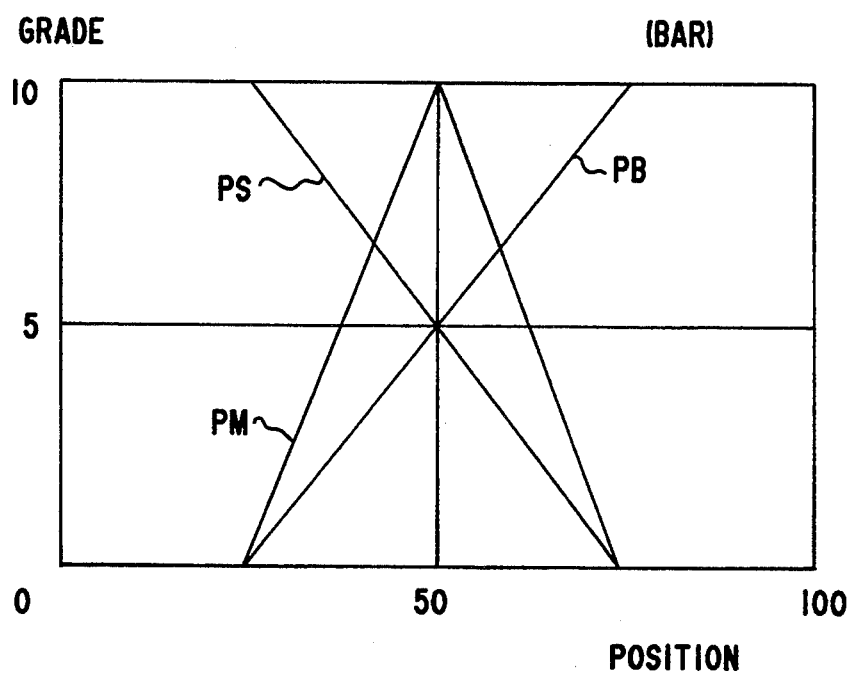
Figure 27:
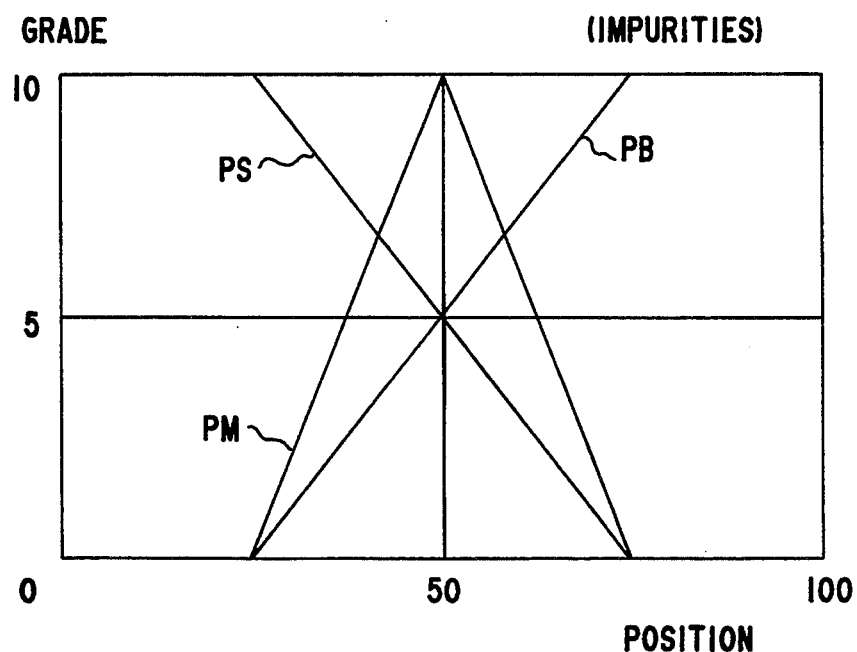
Figure 28:
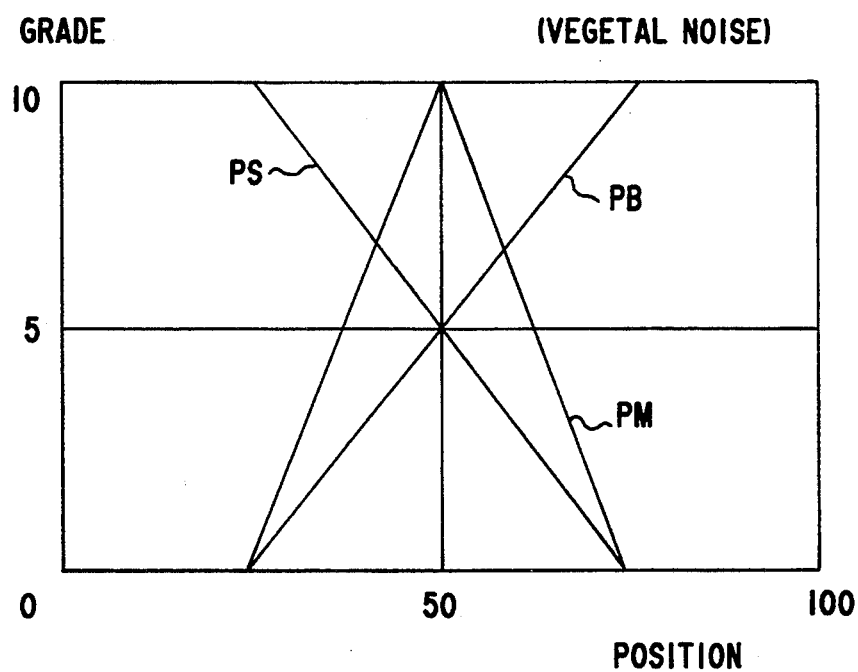

As is clear from the operating flowchart shown in FIG. 9, the data processor classifies the defects of the inspected top sliber 1 according to respective check items based on the amount of the feature stored in the internal memory 18.

FIG. 9 presents the operating flowchart of the data processor 17 when classifying the defects of the inspected wool top sliber. While the initial step of classification is underway, the data processor 17 discerns pillwise defects (including slab, nep, pinpoint, and round trefoil bar symptoms) from vegetal defects (including impurities and bar symptoms). Roundness and slenderness are effectively made available for composing the amount of the feature.

As shown in FIGS. 10 and 11, concretely, the data processor 17 discerns pillwise defects from vegetal defects based on the rating of the roundness and the slenderness by effectively availing of those features including the substantially round shape of the pillwise defect 26 and the slender shape of the vegetal defect 27. Roundness and slenderness are respectively rated by applying the expressions shown herein-below. The data processor 17 executes the classification of the defects by comparing the computed values of the roundness and the slenderness to the predetermined reference values.

Roundness = $4\pi \times$ (area per picture element) $\times$ (total number of picture element)/(peripheral length)$^2$ Slenderness = (area per picture element) $\times$ (total number of picture element)/ ((length of shadow projected against axis $X$)$^2$ + (length of shadow projected against axis $Y$)$^2$ Availing of difference in the light-permeable amount between pills (including slab, nep, and pinpoint) and round trefoil bar, the data processor 17 discerns the pillwise defect from the round trefoil bar based on the gadation discernment and the dispersion discernment. Concretely, values of gradation and dispersion are computed by applying the expressions shown here-below. The data processor 17 classifies the gradation and the dispersion by comparing the values of the gradation and the dispersion to the predetermined reference values.

Gradation = (sum of depth levels)/(total number of picture element)

Dispersion = $(1/n)\Sigma Xi^2 - x^2$ where "n" designates the total number of picture elements;
Xi designates depth levels of picture elements "i"; and
X designates gradation.

Pillwise defects are classified into slab, nep, and pinpoint according to the size. Therefore, pillwise defect is classified into three categories according to area, which is computed by applying the expression shown below.

Area = (area per picture element) $\times$ (total number of picture elements)

The data processor 17 classifies the pillwise defects into slab, nep, and pinpoint, in order of the size, by making a comparison between the computed area value and the predetermined reference value. The data processor 17 further classifies the vegetal defect into impurities, bar, and trefoil bar, by discerning these shapes. Concretely, shape is computed by applying the expression shown below.

Shape = (peripheral length)/$\sqrt{\text{(length of shadow projected against axis } X)^2 + \text{(length of shadow projected against } Y)^2}$ FIG. 12 graphically designates the defect 28 caused by impurities. Assuming that the defect 28 has a peripheral length of about 57, a length "e" of shadow projected against the X axis of 20, a length "f" of the shadow projected against the Y axis, of 20, then the shape of this defect 28 is substantially doubled as per the solution $57/\sqrt{20^2+20^2}$ of the above expression.

FIG. 13 graphically designates the defect 29 caused by a trefoil bar. Assuming that this defect 29 has a peripheral length of about 97, a length "e" of shadow projected against the X axis of 20, a length "f" of the shadow projected against the Y axis of 15, then, the shape of this defect 29 is quadrupled as per the solution $97/\sqrt{20^2+15^2}$ of the above expression. Concretely, the data processor 17 discernibly classifies the defects into those caused by impurities and those caused by trefoil bars by making a comparison between the above numerical values and the predetermined reference values. The data processor 17 discerns impurities from bars based on the measurement of the length. The length is computed by applying the expression shown below.

Length = $\sqrt{\text{(length of shadow projected against axis } X)^2 + \text{(length of shadow projected against axis } Y)^2}$ Incidentally, the defect 28 caused by the impurities shown in FIG. 12 has a length value of about 28, as per the solution to $\sqrt{20^2+20^2}$ from the above expression. The data processor 17 discerns this defect for classification by comparing it to the predetermined reference value. The trefoil bar cited above is eventually added to the category of bar.

In accordance with the operating flowchart shown in FIG. 8 and based on the result of classifying all the defects, the data processor 17 executes the rating of the cleanliness of the inspected wool top sliber. The rated cleanliness is effectively made available for composing the quality standard of the top. The established quality standard is also effectively made available for the composing of basic data when spinning the wool top slibers into yarns in the following processes.

Next, the method of classifying the defects by applying "fuzzy" reasoning is described below.

Initially, based on the definition of a membership function, the data processor 17 establishes a specific range of adjective expressions including "big", "intermediate", and "small" which are respectively applicable to the amount of the features of the defect including roundness, slenderness, area value, shape value, gradation value, length value, and dispersion value, and another specific range of adjective expressions including "high", "normal", and "low" for designating the probability of being a defect. The definition of a membership function may be established in accordance with the judgement of those who are extremely skilled in the related art.

Next, using the range which is applicable to the adjective expressions like "big", "intermediate", and "small" cited above, the data processor 17 defines a "fuzzy rule" for designating the range of the amount of the features of the defect in terms of the relationship between the combination and the probability of being a specific defect, in other words, the data processor 17 defines the "fuzzy rule" which designates the relationship between the conditional terms like "if it were - - - " and the conclusive terms like "probability of - - - " for example.

Table 1 (shown herein-below) concretely designates the membership function and the "fuzzy rule" cited above. For example, if there were a substantial roundness and slenderness, substantial area value, and in addition, more than an intermediate rating of gradation, then, it is highly probable that the defect is caused by the presence of a slab, and therefore, there is less of a probability that the defect is caused by the presence of a pinpoint (p.p.) and noise. Neither a high probability nor a low probability of being a nep, or a trefoil bar, or a bar, is present in the above defect, but the probability is rated to be normal. In this way, relative to the conditional section shown to the left of Table 1, the conclusion section is shown to the right.

Next, the procedure for executing the "fuzzy reasoning" based on the above membership function and the "fuzzy rule" is described below.

Initially, input data is converted in correspondence with the amounts of respective the features of a single defect. Next, adaptability to those adjective terms like "big", "intermediate", or "small", is computed from the membership function. Of the amounts of the features of the defect, if the objective shape is substantially circular, then the roundness is rated to be very close to 1. As mentioned earlier, the shape of a pillwise defect is closer to a circle than that of vegetal defect, and thus, the difference between the pillwise defect and the vegetal defect can be expressed by means of the rating of roundness. The rating of roundness is in a range from 0 to 1. This range is converted into 0 through 100(%). If the objective shape is thinner, then the rating of slenderness approximates 0. Since the vegetal defect has a shape thinner than that of the pillwise defect, the difference between both defects can be designated. The rating of the slenderness is in a range from 0 to 0.5. This range is converted into 0 through 100(%). Substantially, the gradation value represents the mean value of the depth of an object. Since a greater amount of light permeates through the pillwise defect than permeates through the vegetal defect, the pillwise defect generates an image containing a high-level density. The gradation value is in a range from 145 to 170. This range is also converted into 0 through 100(%). The dispersion value represents the unevenness of the depth of objects. Since the amount of light permeating both plant and sliber differs, availing of substantial dispersion of depth level, precision in the classification of trefoil bar can be promoted even when sliber tangles a trefoil bar. The dispersion value is in a range from 0 to 25(%). Like the above cases, this range is converted into 0 through 100(%). The shape value is incremental relative to the increase of shapes of objects by plural number. Since a trefoil bar has shape which is more complex than that of impurities and bars, availing of this complex shape, the difference between trefoil bar and impurities/bar can effectively be designated. The shape value is in a range from 0 to 5. This range is also converted into 0 through 100(%). The area value designates areas of the objects, in which pinpoint (p.p.), nep, and slab, are respectively classified according to their own size, and thus, difference between these can be designated by means of the area value. The area value is in a range from 0 to 100(%). This range is also converted into 0 through 100(%). The length value designates the length of objects. Availing of the length value, the data processor 17 discerns bars (having a minimum of 10 mm of length) from impurities (having a minimum of 3 mm and a maximum of 10 mm of length). The length value is in a range from 0 to 10. This range is also converted into 0 through 100 (%).

FIG. 14 through FIG. 20 graphically illustrate the membership functions of roundness, slenderness, area value, shape value, gradation value, length value, and dispersion value. The label PS shown in these graphic charts designates "small". The label PM designates "intermediate". The label PB designates "big". The label VS designates "very small". The label VB designates "very big". The label PM< shown in the gradation value designates "being greater than intermediate".

TABLE 1

| | | CONTENTS OF FUZZY RULE | | | | | | | | | | | |
|---|---|---|---|---|---|---|---|---|---|---|---|---|---|
| | | CONDITIONAL SECTION | | | | | | CONCLUSION SECTION (PROBABILITY OF BEING DEFECT OF . . .) | | | | | |
| No. | Category | Roundness | Slenderness | Area Value | Shape Value | Gradation Value | Length Value | Dispersion Value | Slab | Nep | Pin Point | Trefoil | Bar | Impurities | Noise |
| 1 | Pillwise Defect | big | big | big | | >intermediate | | | high | normal | low | normal | normal | | low |
| 2 | | big | big | intermediate | | big | | | normal | high | normal | low | | | low |
| 3 | | big | big | small | | big | | | low | normal | high | low | | | normal |
| 4 | | big | big | very small | | very big | | | low | low | low | low | | | high |
| 5 | | big | big | very small | | big | | | low | normal | normal | low | | | normal |
| 6 | | big | big | small | | intermediate | | | | | normal | | | | |
| 7 | | big | big | very small | | intermediate | | | | | normal | | | | |
| 8 | | | | very big | | | | small | high | | | | | | |
| 9 | Vegetal Defect | big | big | very small | | small | | | | | | low | low | normal | high |
| 10 | | small | small | | big | small | | | | | | high | low | low | normal |
| 11 | | small | small | | small | small | big | | | | | low | high | normal | low |
| 12 | | small | small | | small | small | intermediate | | | | | low | normal | high | normal |
| 13 | | small | small | small | small | small | small | | | | | low | low | normal | high |
| 14 | | small | small | very small | small | small | small | | | | | low | low | normal | high |
| 15 | | big | big | very big | | intermedi- | | big | high | | | | | | |

TABLE 1-continued

CONTENTS OF FUZZY RULE

| No. | Category | Round-ness | Slen-derness | Area Value | Shape Value | Gradation Value | Length Value | Dispersion Value | Slab | Nep | Pin Point | Trefoil | Bar | Im-purities | Noise |
|-----|----------|------------|--------------|------------|-------------|-----------------|--------------|------------------|------|-----|-----------|---------|-----|-------------|-------|
| | | | | | | | | CONCLUSION SECTION (PROBABILITY OF BEING DEFECT OF ...) | | | | | | | |

TABLE 2

| Amount of Feature | Example of Input Data | | Adaptability To Words (0 ≦ Adaptability ≦ 10) | | | | |
|---|---|---|---|---|---|---|---|
| | Input Value | Converted Value (%) | | | | | |
| 1. Roundness | 0.24 | 8.0 | small 10.00 | Intermediate 0.00 | Big 0.00 | | |
| 2. Slenderness | 0.09 | 18.0 | small 10.00 | | Big 0.00 | | |
| 3. Area value | 326.00 | 65.2 | very small 0.00 | Intermediate 5.80 | Big 0.00 | Very Big 0.00 | |
| 4. Shape value | 2.19 | 43.8 | small 6.24 | | Big 4.76 | | |
| 5. Gradation value | 135.10 | 0.0 | small 10.00 | Intermediate 0.00 | Big 0.00 | Very Big 0.00 | |
| 6. Length value | 9.54 | 95.4 | small 0.00 | Intermediate 0.73 | Big 8.11 | | |

TABLE 3

ADAPTABILITY OF RULE (RULE NO. 11 AS EXAMPLE)

| No. 11 | CONDITIONAL SECTION ADAPTABILITY | CONCLUSION SECTION ADAPTABILITY |
|---|---|---|
| 1 | Roundness is small: | 10.00 Slab |
| 2 | Slenderness is small: | 10.00 Nep |
| 3 | Area value | |
| 4 | Shape value is small: | 5.24 Pillwise Noise |
| 5 | Gradation value is small: | 10.00 Probability of Being Trefoil Bar is Low |
| 6 | Length value is big: | 8.11 Probability of Being Bar is High |
| 7 | | Probability of Being Impurities is Normal |
| 8 | | Probability of Being Vegetal Noise is Low |
| Adaptability of Rule No. 11 | | 6.24 (Introduces minimum value adaptability in the conditional section) |

TABLE 4

RESULTS OF DEFECT CLASSIFICATION

| | Defect Detection Rate (A/C × 100%) | Defect Discerning Rate (B/D × 100%) |
|---|---|---|
| Total Number of Data | 705 (=C) | 141 (=D) |
| Rate of Achieving Correct Answer Via fuzzy reasoning | 96.0% | 81.6% |
| Rate of Achieving Correct Answer via conventional practice | 96.5% | 62.4% |

A: Number of data which correctly discerned the defets from defect-free objects.
B: Number of data which correctly discerned all defects from each other.
C: Total number of data dealt by the data processor.
D: Number of data which contained all of the designated defects among those which are dealt by the data processor.

FIG. 21 through FIG. 28 graphically illustrate the membership functions of slab, nep, pinpoint, pillwise noise, trefoil bar, bar, impurities, and vegetal noise, which are respectively determined to be the defect. The label PS designating probability indicates "low". The label PM indicates "normal". The label PB indicates "high".

On receipt of the input data designating the roundness and other check items from the image processing signal, the data processor 17 computes adaptability of the adjective words "big", "intermediate", and "small"- 'contained in the input values by applying those values converted from the input data. For example, if the input value of the length value contained in an input data designating a certain defect like bar were 9.54 and the converted value was 95.4, then, as shown in FIG. 29 which designates the membership function of the length value, then the data processor 17 would figure out the adaptability to the term "big" to be 8.11, the adaptability to the term "intermediate" to be 0.73, and the adaptability to the term "small" to be zero (the PS is free of an intersecting point) from the vertical coordinate at the intersecting point of the vertical line of the input value 9.54 against the inclined lines PB, PM, and PS. In the same way, the data processor 17 computes the adaptability to the amount of other features. Table 2 presents an example in which the data processor 17 computes the adaptability to the adjective words in the course of dealing with a variety of defects containing 9.54 of the input length value, 0.24 of the input roundness value, 0.09 of the input slenderness value, 326.00 of the area value, 2.19 of the shape value, and 135.10 of the gradation value.

Next, the data processor 17 computes the adaptability to respective rules by applying the adaptability to the adjective words designating the amount of the features generated by applying those processes described above. For example, Table 3 designates the adaptability to the Rule No. 11 shown in Table 1. Concretely, as shown in Table 3, adaptability of the conclusion section (including the first through seventh conclusions) of the conclusion section of the Rule 11 is arranged to be the minimum value of the adaptability in the conditional section shown to the left of Table 3. In this instance, the minimum value is 6.24.

Figure 30A:
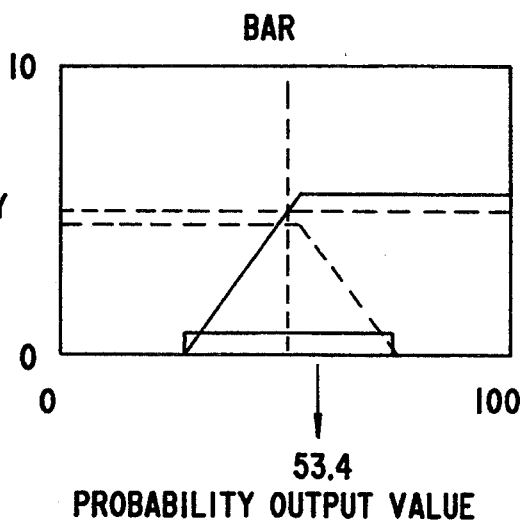
FIG. 30a through 30c illustrate the method of implementing superimposition.
Figure 30B:
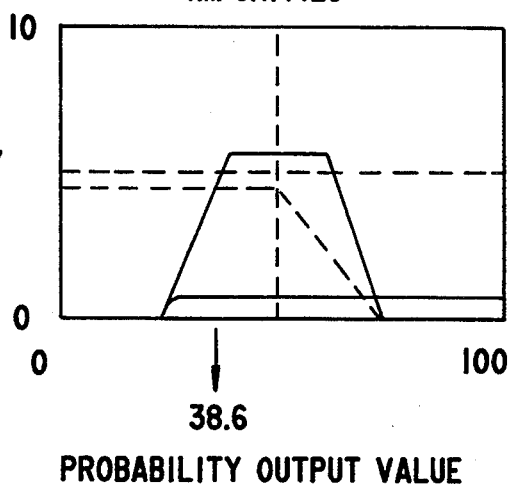
Figure 30C:
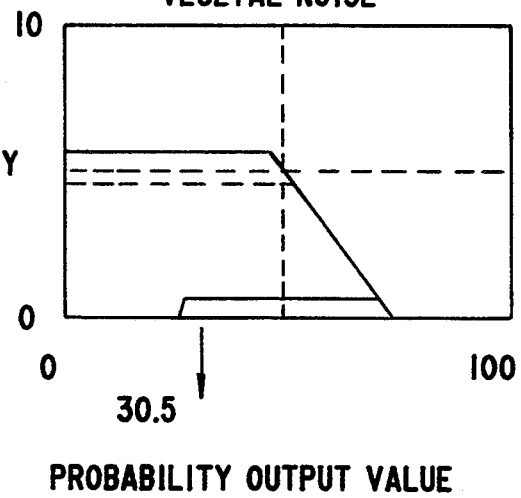

After determining the adaptability of the whole rules as described above, using the determined adaptability, the data processor 17 then executes an operation for computing the minimum membership function of the corresponding conclusion section. Next, the data processor 17 executes an operation for computing the maximum value to determine whether the probability of falling under the respective defects is "high", or "normal", or "low". For example, by referring to the bar-defect determined by the fifth conclusion and based on the adaptability and the computed result, the data processor 17 computes minimum values of PB according to the adaptability value 6.24 of the Rule No. 11, PM according to the adaptability value 0.73 of the Rule No. 12, and PB according to the adaptability value 4.76 of the Rule No. 10. After synthesizing the computed values, the data processor 17 establishes the relationship between the rule adaptability and the probability output value as shown in FIG. 30a. Likewise, FIG. 30a designates the synthesized result of the rule adaptability to defective impurities and FIG. 30b designates the synthesized result of the rule adaptability to vegetal noise.

After completing those operations for computing maximum values, based on the yielded membership function, the data processor 17 computes confirmed values of the probability of being a defect. There are a variety of methods available for computing confirmed values of the probability including application of the center of gravity, the center-computing method, the height-computing method, and the area-computing method. The data processor 17 computes confirmed values of the probability of being a defect by applying more than one of those methods cited above. When computing the probability..output values (confirmed values) of bar, impurities, and vegetal noise based on the application of the center of gravity for example, the confirmed value of the bar defect is determined to be 53.4, the confirmed value of the impurities to be 38.6, and the confirmed value of the vegetal noise to be 30.5. Based on these confirmed values, the data processor 17 concludes that the defect is substantially caused by presence of bar. In the event that the computation of confirmed value yields certain values being equal to each other in two kinds of defects then confirmable answer may be yielded by applying another one of the above computing methods before eventually determining the confirmed value by accepting a majority decision.

Table 4 presents the results of the actually executed top inspection by applying the defect-classifying method via "fuzzy" reasoning. Table 4 also presents the result of inspecting defects based on a conventional method. As is clear from Table 4, although there is no substantial difference in the rate of the detecting of the defect between the results yielded from the conventional method and the method embodied by the invention, the comparative result proves that the rate of yielding a correct answer from the defect discernment based on the "fuzzy" reasoning introduced to the invented method has resulted in noticeable improvement.

As is clear from the above description, since the method embodied by the invention precisely classifies pillwise defects and vegetal defects based on roundness discernment and/or slenderness discernment, the amount of data to be processed in the course of extracting the features of a defect sharply decreases. This in turn permits the method and apparatus embodied by the invention to significantly accelerate the defect inspection with improved data processing efficiency.

Furthermore, as a result of the addition of a gradation discerning process and a dispersion discerning process to the roundness and slenderness discernments, the method and the apparatus embodied by the invention can precisely discern trefoil bar from slab, thus significantly promoting the accuracy of the inspected results.

The method and the apparatus embodied by the invention precisely classifies the pillwise defect further into slab, nep, and pinpoint, by applying an area discernment, and yet, further classifies the vegetal defect into trefoil bar and defects other than the trefoil bar like impurities and bar by applying a shape discernment. The method and the apparatus embodied by the invention further classifies impurities from bar by applying a length discernment. This in turn permits the method and the apparatus embodied by the invention to finely classify defects per check item, thus offering a practical advantage.

Furthermore, when classifying the defects based on the "fuzzy" reasoning, the method and the apparatus embodied by the invention do not respectively identify the defects based on an explicit threshold value, but the invented system solely reasons those defects by applying an ambiguously defined domain, and therefore, the method and the apparatus embodied by the invention can achieve an overall result of judgement which is close to a human judgement. This in turn permits the method and the apparatus embodied by the invention to very precisely discern the confusing plural defects like those of which are actually present in the top sliber.

Figure 31:
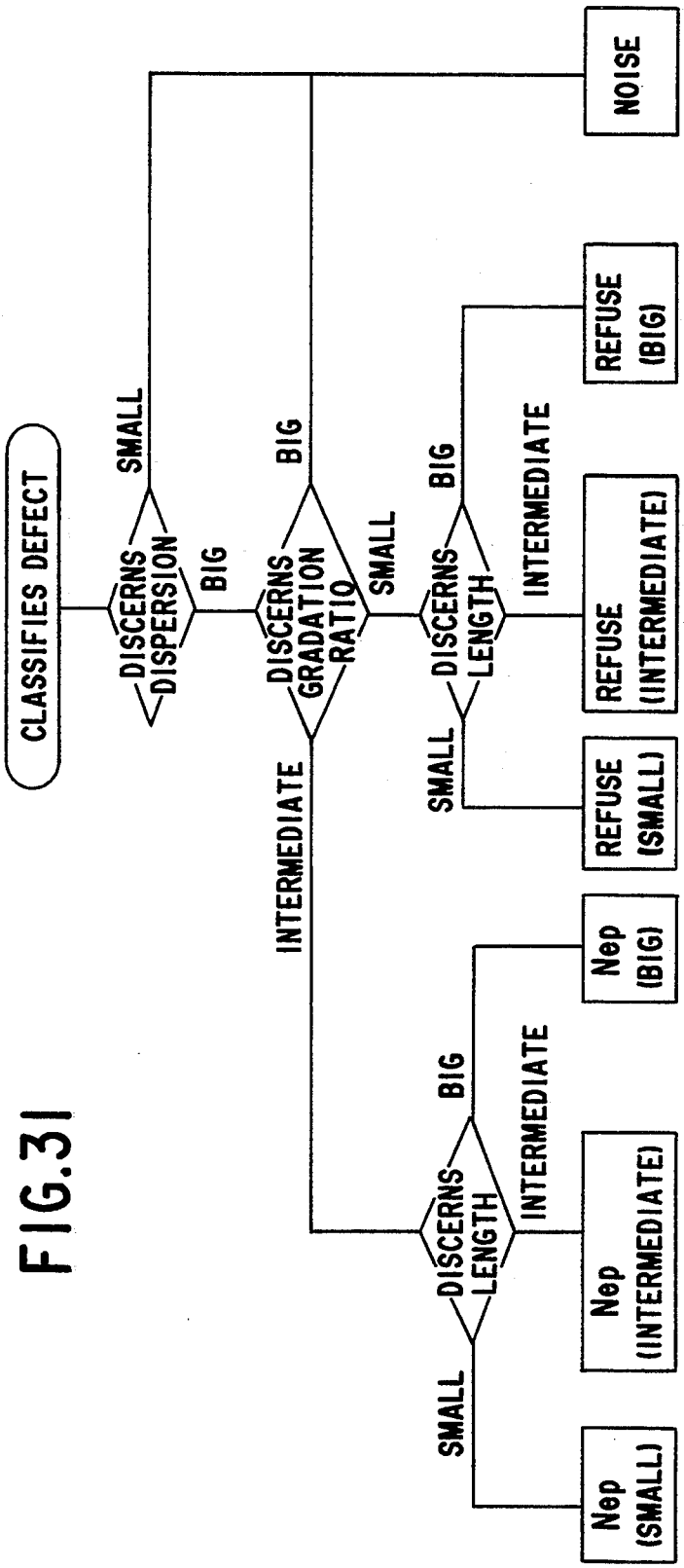
FIG. 31 through 34 presents an operating flowcart of the sequential processes for the classifying of the defects of cotton slibers.

FIG. 31 presents an operating flowchart available for discerning the defects of cotton sliber. The data processor 17 initially executes the dispersion discernment to disperse defects and noise, and then, discerns the defects from each other based on the comparison of the gradation. The data processor 17 discerns the defects based on the comparison of gradation by checking the periphery of a specific area detected by means of a binary code, and then, the periphery of the detected area and the gradation are compared to each other. The defect containing a substantial gradation rate is identified to be noise. The defect containing a negligible gradation rate is identified to be a vegetal mixture, whereas the defect containing a modest gradation rate is identified to be a pillwise defect. There are six kinds of defects inherent in cotton sliber including large, modest, and small vegetal refuse, and large, modest, and small pillwise nep. However, there is little shapewise difference between vegetal refuse and pillwise nep, and yet, unlike wool, there is no difference of size between these. Because of this, when executing a conventional method of classifying the cleanliness of wool top, actually, refuse and nep are often incorrectly discerned from each other.

Figure 32:
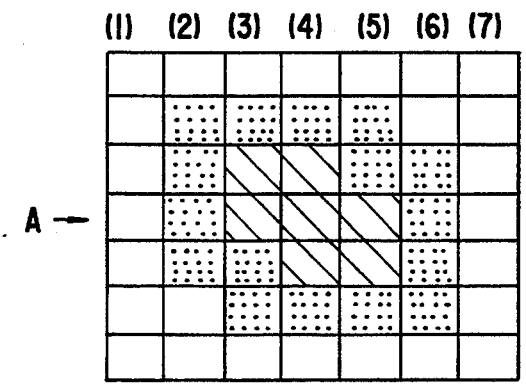
Figure 33:
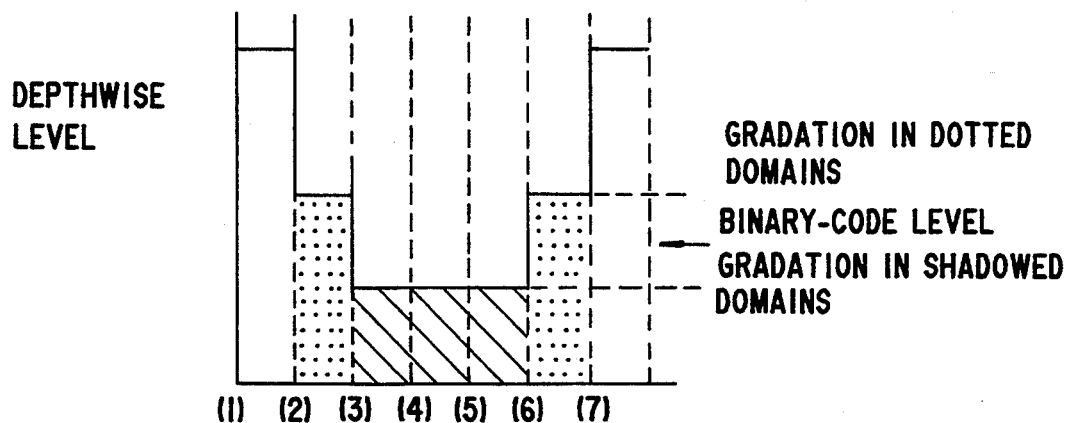
Figure 34:
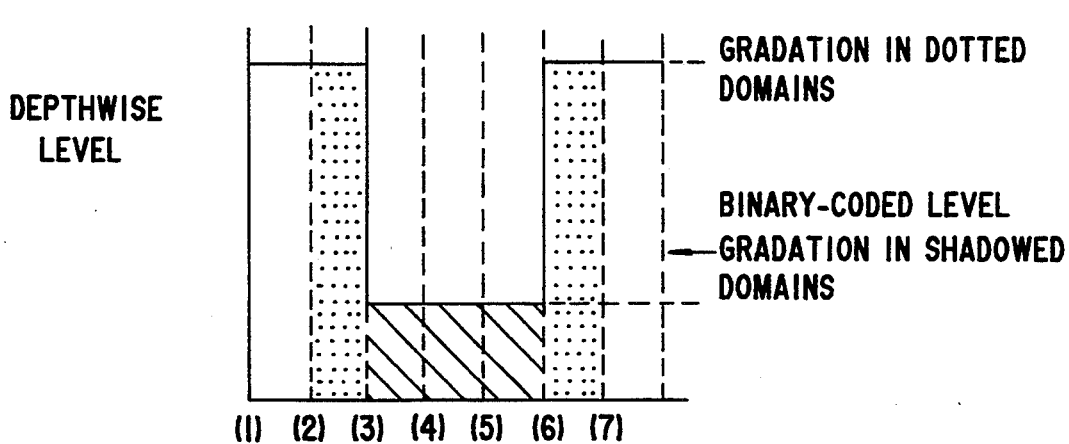

To solve this problem, it is quite effective for the defect inspecting system to introduce the method of discerning the defects based on the comparison of the gradation described above. Concretely, since pillwise defects are generated by tangled fibers, variation of depthwise level from the periphery of defect to the defective domain does not sharply occur unlike the case of a vegetal defect. For example, the image chart shown in FIG. 32 designates distribution of depthwise levels of picture elements on the line indicated by the character A. FIG. 33 designates the distribution of the depthwise levels of a pillwise defect. FIG. 34 designates the distribution of depthwise levels of a vegetal defect. Based on these charts, the following expressions are established.

Gradation =
   (sum of depthwise levels shown in shadowed domain)/
   (the number of picture elements shown in the shadowed domain)
Peripheral gradation ratio =
   (gradation)/[(sum of depth-wise levels in the dotted domains)]/
      [(the number of picture elements in the dotted domains)]

where those values in brackets [] respectively designate gradation of domains in the periphery of defect.

As is clear from the above expressions, the less the difference of the gradation between the defective domain and the peripheral domain, the closer the peripheral gradation ratio to value 1. Therefore, peripheral gradation ratio of a pillwise defect exceeds that of vegetal defect. The method and the apparatus embodied by the invention can precisely discern the pillwise defect from the vegetal defect based on those processes described above. When computing the gradation ratio, the apparatus embodied by the invention initially establishes a proper membership function, and then correctly discerns the pillwise defect from the vegetal defect based on the "fuzzy" reasoning.

Industrial Applicability of the Invention

As is clear from the above description, the method and apparatus for inspecting cleanness of top sliber embodied by the invention precisely and quickly analyzes cleanness of natural fibers like wool and/or cotton with perfect uniformity.

What is claimed is:

1. A method of inspecting the cleanliness of top sliber, comprising the steps of:
   (a) providing a generally planar piece of top sliber;
   (b) providing an electromagnetic wave source proximate said piece of sliber;
   (c) providing an image sensor means for sensing said electromagnetic wave source and for receiving an image of the top sliber;
   (d) generating an image signal of said tip sliber with the image sensor;
   (e) based on said image signal computing (i) gradation discernment of defects and (ii) gradation ratio discernment of the defects;
   (f) classifying the defects into the categories of pillwise defects and vegetal defects mixed in said top sliber based on said computing in step (e);
   (g) computing a length discernment of the defects; and
   (h) further classifying said categories of pillwise defect and vegetal defect into respective defects based on said computing of length discernment of step (g).

2. A method of inspecting the cleanliness of top sliber comprising the sequential steps of:
   (a) generating an image signal by receiving an image of a top sliber with an image sensor;
   (b) based on said image signal, computing: (i) a roundness discernment of a defect on the top sliber, (ii) a slenderness discernment of the defect, (iii) a gradation discernment of the defect, and (iv) a dispersion discernment of the defect;
   (c) classifying the defect into the categories of pillwise defects and vegetal defects mixed in said top sliber based on each of said roundness discernment, slenderness discernment, gradation discernment, and dispersion discernment of step (b).

3. A method of inspecting the cleanliness of top sliber, comprising the sequential steps of:
   (a) generating an image signal by receiving an image of top sliber with an image sensor;
   (b) based on said image signal, computing: (i) a roundness discernment of a defect on the top sliber, (ii) a slenderness discernment of the defect, (iii) a gradation discernment of the defect, and (iv) a dispersion discernment of the defect;
   (c) classifying the defect into the categories of pillwise defects and vegetal defects mixed in said top sliber based on each of said roundness discernment, slenderness discernment, gradation discernment, and dispersion discernment; and
   classifying said category of pillwise defect further into slab, nep, and pinpoint defects by applying area discernment, and classifying said category of vegital defect further into trefoil bar, impurities and bar by applying shape discernment, and further classifying said impurities and bar by applying length discernment.

4. A method of inspecting the cleanliness of top sliber, comprising the sequential steps of:
   (a) providing a generally planar piece of top sliber;
   (b) providing an electromagnetic wave source proximate said piece of sliber;
   (c) providing an image sensor means for sensing said electromagnetic wave source and receiving an image of the top sliber;
   (d) generating an image signal of the top sliber with the image sensor;
   (e) classifying defects on the top sliber into pillwise defects and vegetal defects mixed in said top sliber based on said generated image signal;
   (f) said step of classifying includes the steps of (i) establishing conditional section membership functions for features of defects, (ii) establishing conclusion section membership functions for determining a probability of being a particular defect from said defects, (iii) establishing a fuzzy rule for relating said features of defects with said probability of being a particular defect from said defects; and (iv) classifying the defects based on fuzzy reasoning derived from said conditional section membership functions, said conclusion section membership functions, and said fuzzy rule.

* * * * *